United States Patent [19]

Owen et al.

[11] Patent Number: 4,552,280

[45] Date of Patent: Nov. 12, 1985

[54] CONTAINERS FOR WASTE PRODUCTS

[76] Inventors: William R. Owen, 56 Heol Llanishan Fach, Rhiwbine, Cardiff, CF4 6LF.; Andras Juhasz, 53 Waterloo Rd., Cardiff, CF3 7BJ., both of Wales

[21] Appl. No.: 444,745

[22] Filed: Nov. 26, 1982

[30] Foreign Application Priority Data

Nov. 26, 1981 [GB] United Kingdom .................. 8135733

[51] Int. Cl.4 ................................................. B65F 1/16
[52] U.S. Cl. ..................................... 220/1 T; 206/370; 206/380; 220/329; 220/348
[58] Field of Search ................ 220/1 T, 329, 345, 346, 220/348; 206/63.5, 370, 380; 225/93; 222/510, 511, 515, 518

[56] References Cited

U.S. PATENT DOCUMENTS

| 2,313,428 | 3/1943 | Glenn | 220/348 |
| 3,333,721 | 8/1967 | Marek | 220/345 |
| 3,792,803 | 2/1974 | Kessler | 220/345 |
| 3,972,443 | 8/1976 | Albert | 220/90.4 |

FOREIGN PATENT DOCUMENTS 6508699  1/1967  Netherlands ....................... 206/805

Primary Examiner—George E. Lowrance
Assistant Examiner—Jimmy G. Foster
Attorney, Agent, or Firm—Kemon & Estabrook

[57] ABSTRACT

A container for medical waste products includes a receptacle and a closure member. The closure member is connected to a resiliently deformable member biasing the closure member to close the aperture to the receptacle. In one version the closure member is a cap guided by rails over the surface of the container and having a skeletal outer frame connected to the container which is distorted by opening of the aperture.

There is also disclosed a device for rendering unusable a hypodermic syringe. The device may be provided as a removable insert for the container.

6 Claims, 14 Drawing Figures

CONTAINERS FOR WASTE PRODUCTS

DESCRIPTION

This invention relates to containers. The containers may be particularly suited for receiving waste products.

Bins and containers for receiving waste products are very well known, and a typical domestic waste bin is operated by a pedal which lifts the lid to enable waste to be deposited inside. The lid is usually arranged such that when the operator's foot is removed from the pedal the lid falls under its own weight to cover the opening to the bin. Another type has a pivoted roof portion which can swing about its pivot, in some cases on either side of the pivot, to reveal an entrance to the interior of the bin. The roof portion is pivoted and/or weighted so that it naturally falls back to an equilibrium position covering the entrance to the bin.

Waste disposal bins for hospitals however are required to have additional features which make the normal domestic bins not entirely suitable. One feature is that since the bins may contain contaminated material, they should not have to be emptied by removing plastic lining bags, or by any other operation likely to involve spillage. It is preferable that the bin together with its contents should be incinerated when full. This means that the bin will have to be transported when full, and either of the types of domestic bins described above would be liable to spill its contents if dropped or tilted. Plain cardboard drums have been used in hospitals to receive waste materials, which is introduced through an aperture in the drum. When the drum is to be incinerated the aperture is plugged with a plastics bung. However use of this type of waste container means that while in use there is a direct opening to the contents of the container, and this in unacceptable when contaminated materials are likely to be amongst the contents. It is an object of the present invention to provide a waste disposal container which can be firmly closed for transportation and normally closed when in use but still able to be opened for use without difficulty.

According to the present invention in a first aspect there is provided a container comprising a receptacle having an aperture through which articles are deposited in the container, a closure member secured to the receptacle and constrained for movement between first and second positions at which the aperture is opened and closed respectively, and means for releasably securing the closure member in its second position comprising a resiliently deformable member, engaged with the receptacle such that it has to be deformed against its resilience to move the closure member from its second position.

In one embodiment of the invention the closure member comprises a movable cap having forward and rear ends, and constrained by guide means for movement across a surface of the receptacle containing said aperture, the forward end being that which precedes as the closure member is moved from the first to the second positions, the resiliently deformable member being connected to the movable member and secured to the receptacle.

In an alternative embodiment of the invention the closure member comprises a shutter rotatably mounted on the container and rotatable between said first and second position.

The resiliently deformable member may comprise a container as aforesaid wherein the resiliently deformable member comprises an elongate member connected with the shutter at a first end, and in contact with a wall of the container the axis of rotation of the shutter relative to the wall of the container being located such that as the shutter is rotated towards its first position the distance between its first end and said wall is reduced causing the member to be increasingly bent against its resilience so that it produces a restoring force bending to force the shutter to its second position.

The invention in a second aspect provides, a device for rendering unusable a hypodermic syringe or similar article comprising a body member, and one or more blades supported for slicing movement beneath the plate member, the body member having at least one aperture dimensioned to receive the needle or barrel portion of the syringe such that by operating said one or more blades the needle or portion of the syringe is crushed or severed.

The device may be included as a removable insert in the aperture of the container.

Embodiments of the invention will now be described, by way of example only, with reference to the accompanying drawings.

Referring to the figures, a waste disposal container for medical waste products if formed from three interfitting parts. These parts are a drum 1 which forms the base of the container, a lid 2 and a closure cap 3.

Figure 1:
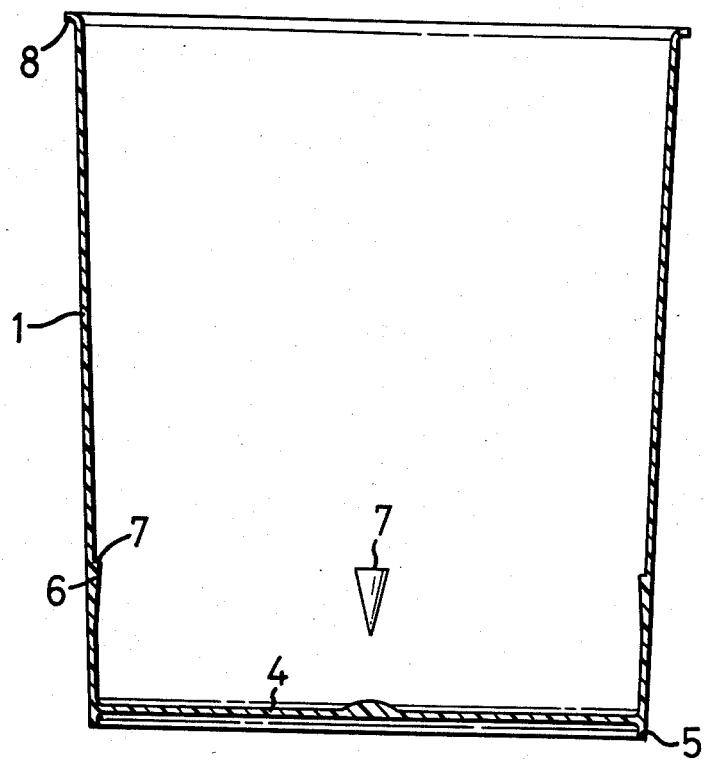
FIG. 1 is an axial sectional view through a drum forming the base of a waste disposal container.

Referring in particular to FIG. 1, the drum 1 is a thin walled, hollow structure of circular cross-section, and is sightly tapered from top to bottom. The narrower end of the drum is closed by an integrally formed base wall 4 whose inward-facing surface forms the bottom of surface of the container. The side wall of the drum 1 extends by a small amount beneath the base wall 4 to form an annular flange 5 on which the container stands when in use. The inner surface of the side wall of the drum 1 has integrally formed therewith at a short distance up from the base wall 4, four-equally spaced lugs 6 of wedge-shape cross-section, disposed such that the each presents a narrow circumferential ledge 7 facing the open upper end of the drum. This enables another drum to be stacked with its base resting on the ledge 7.

At the open, wider end of the drum the side wall is bent outwardly to give a narrow, circular lip 8 the funtion of which is to engage the lid 2, as is described below.

Figure 2:
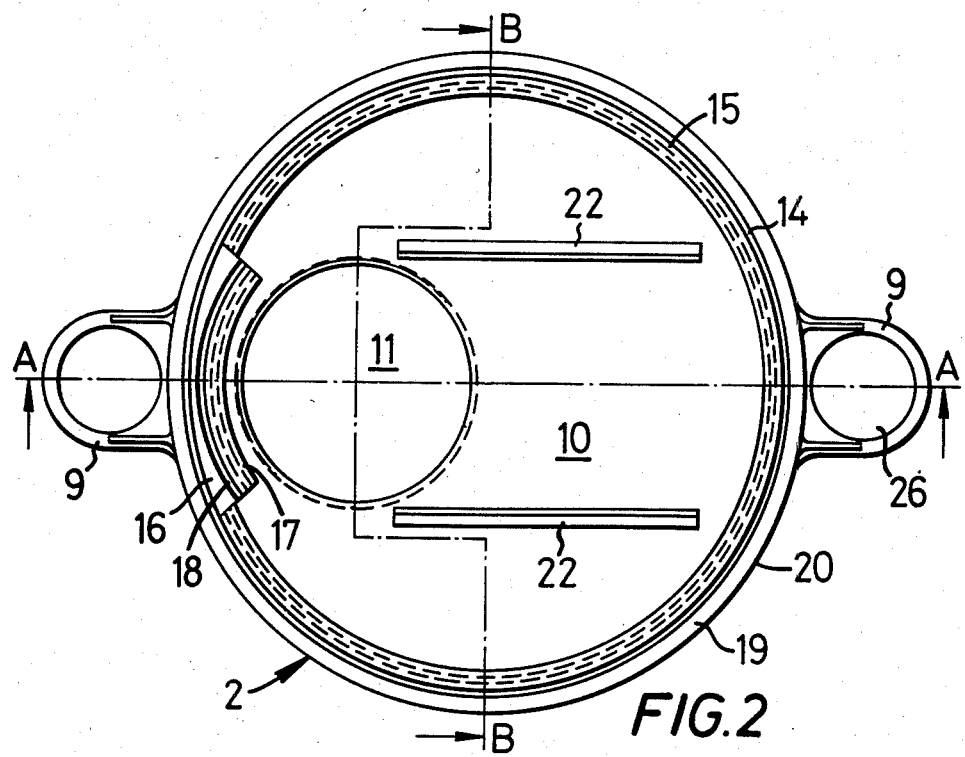
FIG. 2 is a plan view of the lid for the drum.
Figure 3:
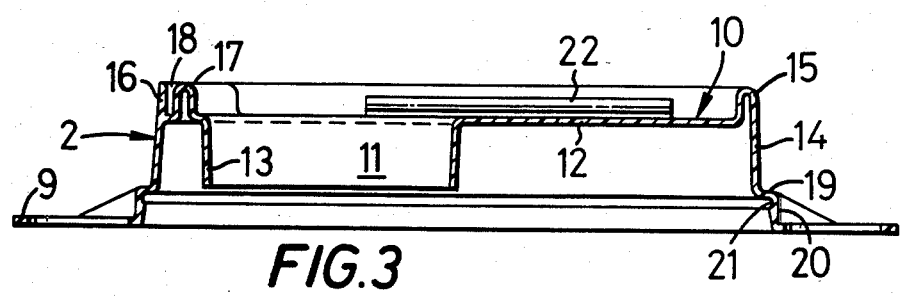
FIG. 3 is an axial sectional view through the lid of FIG. 2 along the line A—A.
Figure 4:
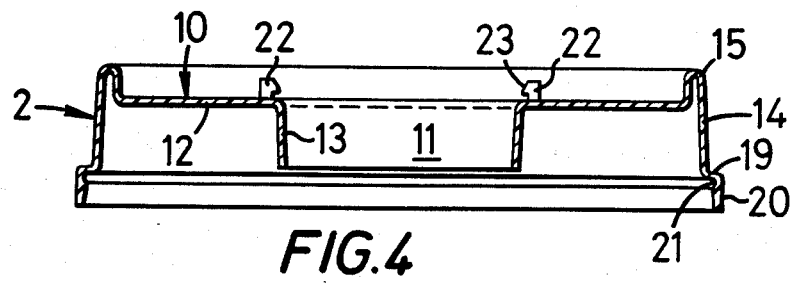
FIG. 4 is an axial sectional view through the lid of FIG. 2 along the line B—B.
Figure 6:
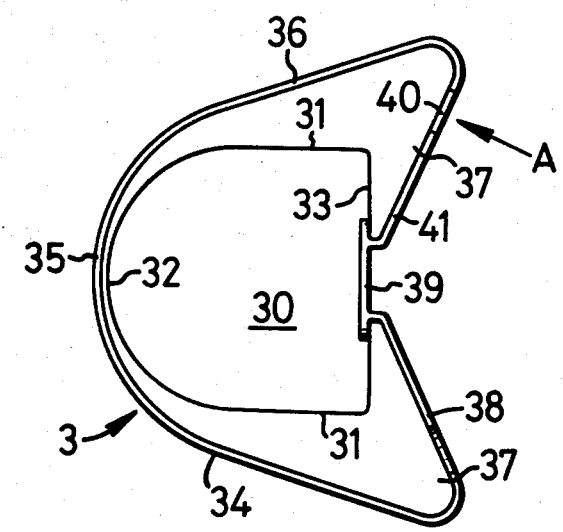
FIG. 6 is a plan view of a closure cap for the lid.
Figure 7:
FIG. 7 is an end elevation view of the closure cap.
Figure 8:
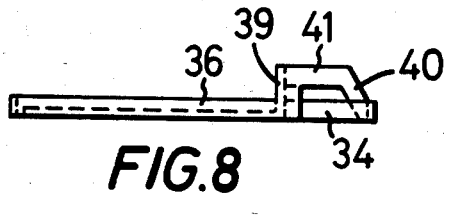
FIG. 8 is a side elevation of the closure cap.
Figure 9:
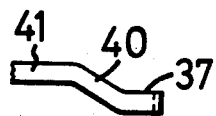
FIG. 9 is a scrap view in the direction arrow A.

Referring now to FIGS. 2, 3 and 4, the lid 2 is generally circular in plan with two lugs 9, described in more detail below. The transverse surface 10 of the lid is generally circular in plan and in half of its surface it includes a circular aperture 11 through which waste products are introduced into the assembled container. The aperture 11 is located between a position close to a diameter of the transverse surface 10 and a position a small distance from the edge of the surface 10. The transverse surface 10 is the upper surface of a wall made of polypropylene or other suitable plastics material 12 which is integral with an annular skirt 14, perpendicular to the surface 10 and extending downwards along the periphery of the circular aperture 11. The side wall 14 of the lid 2 is integrally moulded with the upper wall 12. The upper wall 12 and the side wall 14 are joined by an upstanding flange 15 comprising a portion extending upwardly from the periphery of the upper wall 12 which is smoothly curved at its upper end and folded back on itself, and is then continuous with the circumferential side wall of the lid 2. Thus the upstanding flange 15 has a double thickness of material separated by a small channel. The upstanding flange 15 extends around the greater part of the circumference of the transverse surface 10 of the lid, apart from a region of the circumference adjacent the radially outer edge of the circular aperture 11. In this region of the periphery of the transverse surface of the lid the two walls of the upstanding flange 15 reduce to a single, thicker wall 16. The thickness of the wall 16 varies along its length so that its radially inner surface is coaxial with the aperture 11.

Between the wall 16 and the edge of the circular aperture 11 the upper wall 12 of the lid is subject to a upward fold to that an arcuate double-walled ridge 17 is located between the wall 16 and the aperture 11. The ridge 17 has the same height as the wall 16 and is disposed along a circular arc co-axial with the circular aperture 11. The ridge 17 extends along an arc subtending approximately 80° and defines an arcuate channel 18 between itself and the wall 16. The channel 18 is thus also disposed along an arc co-axial with the circular aperture 11 and subtends an angle of 80°. The upper parts of the wall 16 and ridge 17 facing inwards towards the slot 18 are slightly thickened so that the slot is of reduced width adjacent its open end.

The circumferential side wall 14 of the lid extends downwardly from the upstanding flange 15, or from the single-thickness wall 16 in the region adjacent the circular aperture 11 and is tapered so that the diameter of the lid increases towards at its lower edge. Nearer the lower end of the circumferential side wall 14 the wall projects outwardly to form a step 19 so that the diameter of the lid within the portion 20 of the side wall 14 below the step is greater than the diameter of the lid in the region above the step. The lower wall portion 20 reduces in thickness from below the step to its lower edge, but just adjacent the step 19 it has a small circumferential recess 21 which is adapted to receive the rim of the drum portion of the container.

Two elongate rails 22 are located on the transverse surface 10 of the upper wall 12 of the lid. These rails 22 are parallel and their inner facing edges are generally tangental to the edge of the circular aperture 11. The rails 22 extend from just short of the periphery of the lid on the side opposite the single-thickness wall 16 and channel 18 and terminate just short of that diameter of the circular aperture 11 which is perpendicular to the length of the rails. The sides of the rails 22 upstanding from the transverse surface 10 and facing each other across the surface are contoured to provide engagement strips 23, FIGS. 4 and 5, which are adapted to engage the closure cap of the container as is further described below.

Figure 5:
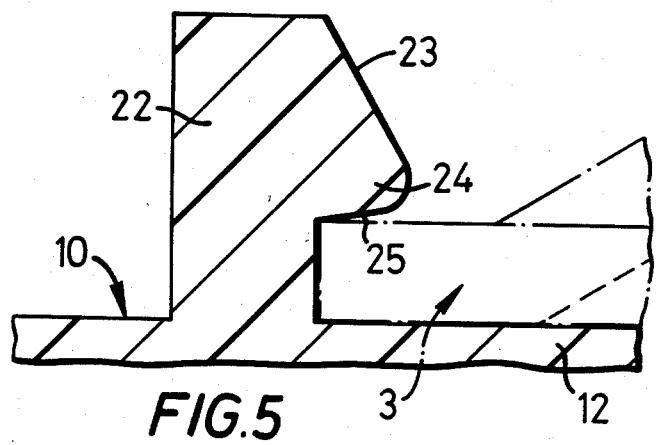
FIG. 5 is an enlarged part of the sectional view of FIG. 4.

FIG. 5 shows, in enlarged scale, one of the rails 22 and illustrates the engagement strip 23 which is formed by an angled protuberance 24 from the top edge of the rail to provide the inwards-facing wall of the rail with a 30° slope. This angled surface terminates approximately one third of the way down the inwards-facing surface of the rail and is smoothly rounded and continuous with the under surface 25 of the engagement strip. The under surface 25 is at an angle of 100° to the upstanding side surface of the rail and is therefore slightly upwardly inclined. The under surface 25 forms an abutment surface to maintain the closure cap 3 in position.

The lugs 9 extend from the outer periphery of the lid at diametrically opposite positions. One of the lugs is symmetrically disposed adjacent the single-thickness wall 16 so that the lugs 9 are also diametrically disposed with respect to the circular aperture 11. Each lug is a flat transverse projection from the lower edge of the circumferential side wall 16 and each lug encloses a circular aperture 26 which occupies the major part of its area. The lugs 9 are used for lifting the container and also prevent the container from rolling if knocked over.

Referring now to FIGS. 6, 7, 8 and 9, the closure cap 3 comprises a cover plate 30 having a pair of parallel sides 31 and a semi-circular front end 32 and a rectilinear rear edge 33. The cover plate 30 has a configuration adapting it to cover the circular aperture 11 in the lid 2. The cover plate is fixed within a skeletal outer frame 34. The frame 34 is a narrow strip of low density polypropylene disposed edge-on with respect to the plane of the cover plate 30. The outer frame 34 has an arcuate frontal portion 35 with a radius somewhat greater than the semi-circular front end 32 of the cover plate 30 and is situated forward of the front end of the cover plate and spaced therefrom by a narrow gap. The sides 36 of the outer frame diverge towards the rear of the cover plate and extend rearwardly beyond the rear edge of the cover plate. At their rear extremities the sides of the frame turn inwards and forwards to form two sweptback wings 37. The in-turned parts 38 of the wings are connected above the rear edge of the cover plate by a rectangular plate 39 upstanding from the rear edge 33 of the cover plate As can be best seen from FIGS. 7 and 8, the wings 37 are not coplanar with the front portion of the skeletal frame 34; the in-turned parts 38 include a upwards sloping portion 40 at a position spaced inwardly of the arcuate tips of the wings. The edges of the inner portion of each in-turned part 38 of the wings are horizontal and the inner portions 41 are bent at their ends to join the plate 39 perpendicularly.

The container is assembled by pressing the lid 2 over the open end of the drum 1. The lip 8 around the upper edge of the drum gives the drum a slightly wider diameter than the internal radius of the lower wall portion 20 of the lid so that as the lid is pushed down it is resiliently deformed as the lip 8 is pressed between the thicker parts of the lower wall portion 20 until it engages in the circumferential recess 21, where it engages as a snap fit.

The closure cap 3 is fitted onto the lid 2 by pressing the cover plate 30 between the engagement strips 23. This action resiliently deforms the rails 22. The arcuate frontal portion 35 of the outer frame of the closure cap is positioned in the slot 18.

To reveal the aperture 11 the cover plate is pulled away from the ridge 17, and the arcuate frontal portion 35 of the frame remains in the sot 18. The cons-consequent resilient deformation of the skeletal frame 34 produces a returning force tending to return the cover plate to a position in which it completely covers the aperture 11. The cover plate 30 can move forwards and backwards within the rails 22 between a position where it covers the aperture 11 to a position where the whole of the aperture is opened.

The pulling movement necessary to open the aperture 11 is accomplished by pressing against the plate 39 thus deforming the wings 37 of the skeletal frame. The cap, and in particular the frame portion, is of a size such that a user can conveniently pull the frame rearwardly by means of his thumb and forefinger so that opening and closing can be accomplished with the use of one hand only. An item for disposal can therefore be held in the free hand whilst the aperture is opened. It will be appreciated that this is particularly advantageous since it enables the user to complete the waste disposal operation without having to rest the, possible infected, waste article on any other surface.

The container can thus be repeatedly opened and closed during use so that when only partially full does not normally present an opening from the interior to the local environment. The same resilient closure mechanism is also used when the bin is subsequently carried away for incineration and therefore there is a significant economy in the mechanisms that need to be employed.

Figure 10:
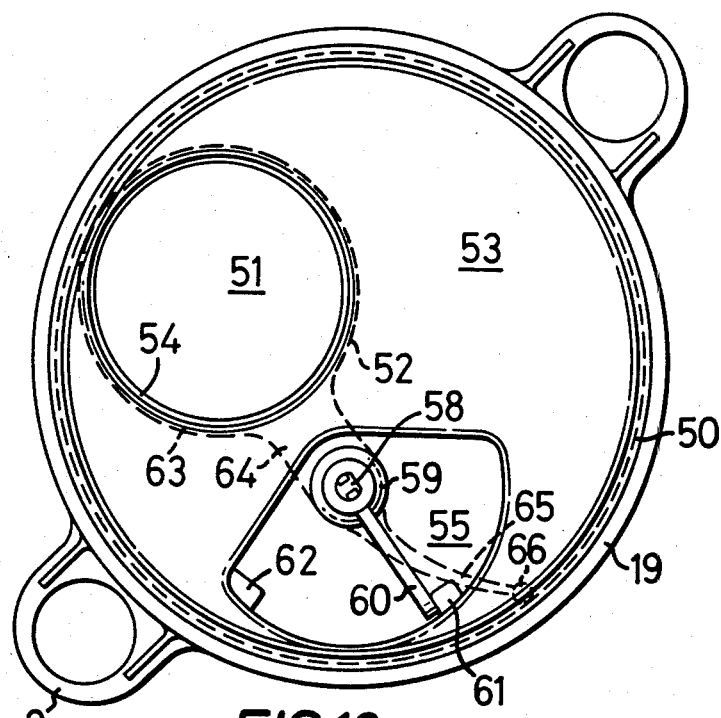
FIG. 10 is a plan view of a lid for a container in accordance with a second embodiment of the invention.
Figure 11:
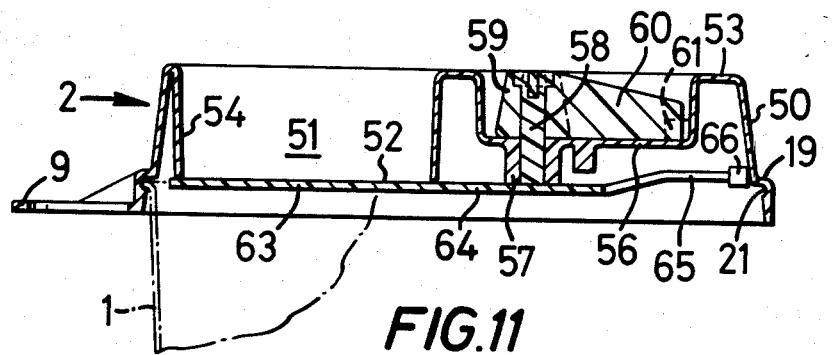
FIG. 11 is an axial sectional view of the lid of FIG. 10.

FIGS. 10 and 11 show a second embodiment of the invention which uses a drum for the base of a container as in the above described embodiment. The second embodiment also includes a lid 2 having a circumferential side wall 50 whose lower portion is identical to that described in the preceding embodiment, that is to say it includes the step 19 and the recess 21 so that the engagement between the lid and the base is as described above. The two lugs 9 are also included and are identical to those described above. In this second embodiment however, in contrast to the first described, a circular aperture 51 is closed by rotating shutter 52. The upper portion of the circumferential side wall 50 is approximately 3 times the height of the lower portion and is tapered towards this other extremity. The upper wall 53 of the lid is formed integrally with the circumferential side wall 50 and around the circular aperture 51 the upper wall 53 is bent downwardly to provide an annular skirt 54 extending downwards to the height of the step 19 in the side wall. The upper wall 53 of the lid, in addition to being folded to surround the circular aperture 51 is also bent downward around the edge of a sectorial-shaped depression 55 in the upper surface of the lid. In addition to forming a skirt extending downwardly from the transverse parts of the upper wall the upper wall also continues integrally with the lower edges of the skirt to form a base platform 56 defining the floor of the depression 55. The height of the base platform 56 is approximately mid way between the step 19 and the upper extremity of the circumferential side wall 50.

The depression 55 is located such that its axis of symmetry is co-linear with a diameter of the aperture 51 and this axis is offset from the centre of the circular lid. The disposition of the depression 55 is such that its arcuate portion is furthest from the circular aperture and its sector subtends a angle of approximately 125°. Near the apical portion of the depression 55 the base platform 56 has a boss 57 moulded integrally therewith and extending downwardly from its upper surface to a depth just equal to the extremity of the skirt 54 around the circular aperture 51. The boss 57 has rotatably-mounted through it a polypropylene spindle 58. The spindle 58 carries a frusto-conical knob 59 being flush with the upper surface of the base platform 55. The knob 59 has a laterally extending wing 60 extending outwardly almost to the skirt along the arcuate portion of the depression 55. From its root the upper edge of the wing 60 slops downwardly to its extremity. A pair of small blocks 61 and 62 are integrally formed on the inward facing surface of the skirt along the arcuate portion of the depression 55. The block 61 is situated just to one side of the axis of symmetry of the sectorial-shaped depression and the block 62 is situated at one end of the arcuate portion.

The shutter 52 which closes the aperture 51 comprises circular base portion 63 having a radius which is greater by a small amount than the aperture 51, and a laminar tongue 64 extending coplanar with the circular plate 63 from the circumferential edge thereof. The shutter 52 is disposed beneath the skirt 54 around the aperture 51 and in a closed position the circular plate 63 is flush with the lower edges of the skirt 54 and completely covers the opening into the interior of the container. The tongue 64 extends from the plate 63 and is fixed to the lower end of the spindle 58 so that as the spindle is rotated the shutter 52 is rotated in a horizontal plane about the axis of the spindle, and when moved in a clockwise direction it is removed from its position obturating the aperture 51. The free end of the tongue 64 has extending therefrom in a direction away from the plate 63 a resilient polypropylene tail 65 which has a length greater than the distance between the end of the tongue 64 and the circumferential wall of the lid. The tail 65 includes along its length an upward sloping portion so that the tail 65, at its free end bears against the inner surface of the circumferential side wall 50 just above the step 19. At its free end the tail 65 has a knob 66 which makes a sliding engagement with the inner surface of the side wall 50. To accommodate its length the tail 65 is curved and under tension and is curved in such a direction that as the shutter 52 is rotated in a clockwise direction it is dragged along behind. The offset location of the spindle 58 on the surface of the lid means that as the shutter 52 is rotated in a clockwise direction the space between the spindle and the circumferential side wall 50 occupied by the tail 65 gets narrower. Thus the tension and hence the restoring force produced by the tail 65 increases as the shutter is away from its closed position. Thus in use an operator rotates the spindle 58 by operating the wing 60 on the knob 59 to move the shutter 52 beneath the aperture 51 in a clockwise direction thereby to gain an entrance to the container beneath. The block 62 limits the extent of this rotation when waste products have been deposited through the aperture 51 and the wing 60 is released the resilience of the tail 65 causes the shutter to rotate in an anti-clockwise direction until the wing 60 is obstructed by the block 61 on the skirt of the depression 55. The location of the block 61 is such that when it obstructs the wing 60 in this position the circular plate 63 is disposed beneath the aperture 51 and seals it.

Figure 12:
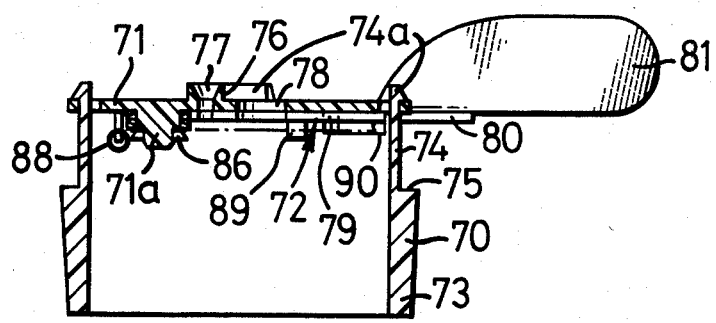
FIG. 12 is an axial section through a device for crushing syringes.
Figure 13:
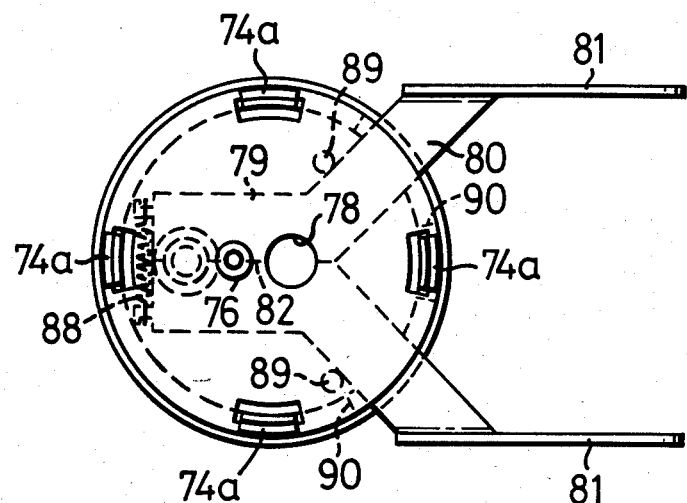
FIG. 13 is a plan view of the device of FIG. 12.
Figure 14:
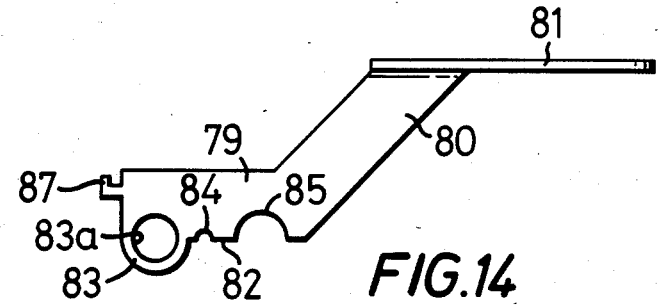
FIG. 14 is a plan view of one blade incorporated in the crusher device.

Referring to FIGS. 12 to 14 a crusher device for use with the waste disposal bin described with reference to FIGS. 1 to 9 comprises a barrel 70, a cover plate 71, and a pair of stainless steel slicing arms 72. The device is adapted to fit as an insert in the circular aperture 11 in the lid of the bin. The barrel 70, moulded from copolymer polypropylene, is generally cylindrical in shape. The wall of the barrel comprises lower and upper cylindrical portions 73 and 74, the former being thinner than the latter. The inner surfaces of the two portions are flush so that an annular step 75 results on the outer surface. The thickness of the lower portion 73 tapers slightly in a downwards direction and the external diameter of the barrel at its lower extremity is approximately equal to that of the lower periphery of the skirt 13 around the aperture 11. The barrel may thus be push-fitted into the aperture 11 so that the step 75 is flush with the transverse surface 10 of the lid of the bin.

The cover plate 71 is circular in outline and has four equiangularly-spaced arcuate slots near its periphery and centred about the centre of the plate. Four corresponding lugs 71a at the upper periphery of the upper portion 74 of the barrel enable the cover plate to be securely fixed to the barrrel. An integral boss 76 upstands from the surface of the cover plate and has a bore 77 arcuately tapering from an upper entrance opening to a lower narrow outlet. The cover plate has a further entrance aperture 78 to one side of the boss 76. On the other side of the boss, in line with the boss and the aperture 78 is a downwardly extending peg 83, about which the slicing arms 72 are rotatably mounted.

The two slicing arms 72 each comprise a horizontal, flat stem portion 79, and outwardly-angled portion 80, and a lateral, operating plate 81 upstanding from the end of the angled portion 80. The longitudinal axis of the operating plate 81 being parallel to, but spaced outwardly from the stem portion 79. The longitudinal edge 82 of the stem portion that is remote from the operating plate 81 has a projecting ear 83 adjacent its free end. The ear 83 partially surrounds a circular aperture 83a through the stem portion. Spaced from the ear 83 the edge 82 has a small semi-circular recess 84 and further spaced therefrom another, larger, semi-circular recess 85.

The two arms 72 are oppositely handed and are aligned beneath the cap such that their edges 82 are aligned, but with one arm being slightly above the other so that by moving the arms horizontally a slicing action takes place.

The arms are mounted by inserting the peg 83 through the overlapping apertures 83a in the arms. A washer and spire fixing 86 retains the arms on the peg enabling them to pivot thereon.

At the free end of each stem portion 79 the arms include a bent tab portion 87. A tension spring 88 is interposed between the tab portions 87 forcing the angled portions outwardly against respective stops 89 extending downwards from the undersurface of the cap. The extent of the arms is accommodated by a circumferential slot 90 through the upper wall portion of the barrel extending in an arc subtending the same angle as the stops 89.

The device is used to crush used syringes. It is located in the aperture 11 in the lid of the bin by fully retracting the cover plate 30. When released, the cover plate abuts against the outer surface of the upper wall of the barrel. In this position the cover plate 30 overlaps the step 75 preventing the barrel from being removed, unless by withdrawal of the cover plate. The device is used by inserting a used syringe through the boss 76 so that the needle projects through the hole formed by the two semi-circular recesses 84. The operating plates 81 of the arms are then squeezed together shearing the needle. When released, the arms are forced back against the stops by the action of the spring 88. The syringe is then withdrawn and re-inserted through the entrance aperture 78 in the cap and then through the underlying hole formed by the semi-circular recesses 85 in the arms. By squeezing the arms the nozzle of the syringe is severed.

It will be appreciated that by means of these two operations the syringe is rendered completely useless. Once the waste bin is full the crusher device can be removed, cleaned and sterilized and repeatedly reused.

We claim:

1. A self-closing container for waste or contaminative articles comprising
    a receptacle having an aperture through which articles are deposited in the container and a retaining projection,
    a closure member secured to the receptacle and constrained for rectilinear sliding movement across the plane of the aperture between first and second positions at which the aperture is opened and closed respectively,
    and means for releasably securing the closure member in its second position comprising a substantially non-stretchable, resiliently deformable band, engaged around said retaining projection on the receptacle and joined at both ends to the closure member and extending around the periphery of the closure member such that it has to be deformed against its resilience to move the closure member from its closed position, the resiliently deformable band having a first preset natural shape and predisposition, when the closure member is in its closed position, and a second shape, when the closure member is in its open position, which is a distortion of the first shape and from which the deformable band naturally returns to said first shape to close the container.

2. A self-closing container as claimed in claim 1 characterised in that the closure member and the resiliently deformable band are formed as a single element.

3. A self-closing container as claimed in claim 2 characterised in that the single element comprising the closure member and resiliently deformable band is composed of a single material.

4. A container as claimed in claim 1 including an operating surface joined to the closure member and upstanding therefrom, the operating surface being adapted for use by an operator to apply pressure by hand to move the closure member from its second position.

5. A container as claimed in claim 1 wherein the closure member is constrained for movement between said first and second positions by a pair of guide rails on the surface of the container.

6. A container as claimed in claim 5 wherein at least a postion of the resiliently deformable band is raised above the height of the guide rails to accommodate said movement of the closure member.

* * * * *